(12) United States Patent
Murphy

(10) Patent No.: US 11,717,200 B2
(45) Date of Patent: Aug. 8, 2023

(54) ERGONOMIC SUCTION SYRINGE AND METHODS OF USE

(71) Applicant: Timothy Murphy, Providence, RI (US)

(72) Inventor: Timothy Murphy, Providence, RI (US)

(*) Notice: Subject to any disclaimer, the term of this patent is extended or adjusted under 35 U.S.C. 154(b) by 258 days.

(21) Appl. No.: 16/784,584

(22) Filed: Feb. 7, 2020

(65) Prior Publication Data

US 2021/0244324 A1  Aug. 12, 2021

(51) Int. Cl.
*A61B 5/15* (2006.01)
*A61B 5/153* (2006.01)

(52) U.S. Cl.
CPC ........ *A61B 5/150244* (2013.01); *A61B 5/153* (2013.01); *A61B 5/15003* (2013.01); *A61B 5/150221* (2013.01); *A61B 5/150236* (2013.01); *A61B 5/150389* (2013.01); *A61B 5/150519* (2013.01)

(58) Field of Classification Search
CPC .............. A61B 5/153; A61B 5/150159; A61B 5/150389; A61B 5/150244; A61B 5/150236; A61B 5/150221; A61B 5/15003
See application file for complete search history.

(56) References Cited

U.S. PATENT DOCUMENTS

| | | |
|---|---|---|
| 3,566,859 A | 3/1971 | Schwartz |
| 3,747,812 A | 7/1973 | Karman |
| 3,872,864 A | 3/1975 | Allen |
| 4,312,344 A | 1/1982 | Nilson |
| 4,766,908 A | 8/1988 | Clement |
| 4,861,335 A | 8/1989 | Reynolds |
| 5,176,642 A | 1/1993 | Clement |
| 5,354,285 A | 10/1994 | Mazurik |
| 5,549,573 A | 8/1996 | Waskonig |
| 5,891,052 A | 4/1999 | Simmons |
| 6,245,046 B1 | 6/2001 | Sibbitt |
| 7,806,858 B2 | 10/2010 | Smith |
| 8,088,104 B2 | 1/2012 | Smith |
| 9,101,713 B2 | 8/2015 | Cowan |
| 2005/0192543 A1 | 9/2005 | Sibbitt |
| 2007/0032743 A1 | 2/2007 | Hibner |
| 2010/0324484 A1 | 12/2010 | Smith |
| 2013/0126559 A1 | 5/2013 | Cowan |
| 2016/0151570 A1 | 6/2016 | Rhinehart et al. |
| 2019/0029657 A1 | 1/2019 | Gulev et al. |
| 2020/0046276 A1* | 2/2020 | Valentino ............ A61M 5/3216 |

FOREIGN PATENT DOCUMENTS

WO   WO-2020221381 A1 * 11/2020

OTHER PUBLICATIONS

Randy R. Sibbitt, Wilmer L. Sibbitt, Jr, Sharon E. Nunez, Lawrence G. Kettwich, Sharon C. Kettwich, and Arthur D. Bankhurst. Control and Performance Characteristics of Eight Di.

(Continued)

*Primary Examiner* — Daniel L Cerioni

(57) ABSTRACT

An ergonomic suction syringe and method for performing medical procedures in which suction is generated and can be delivered to a medical device by a single-handed compression motion, with suction actuated by forward motion of a piston into a cylinder, and in which suction can be maintained essentially permanently once activated without any further effort by the operator, even hands-free.

12 Claims, 13 Drawing Sheets

(56) References Cited

OTHER PUBLICATIONS

Christopher J. Foster, Robert J. Teskey, Catherine M. Kells, Blair J. O'Neill, Nancy Fitzgeralld, Kim Foshar, Cathy Peck. Does the speed of balloon deflation affect the compli.
Alberts MB1, Shalit M, LoGalbo F.Ann Emerg Med. Feb. 2004;43(2):181-6. Suction for venomous snakebite: a study of "mock venom" extraction in a human model.

* cited by examiner

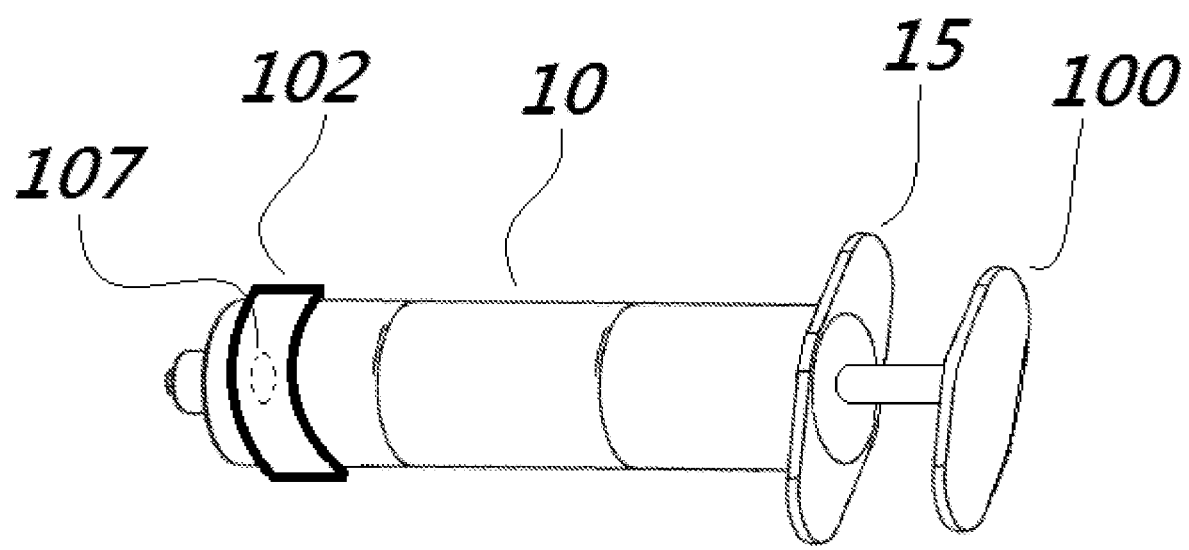

FIG. 16A
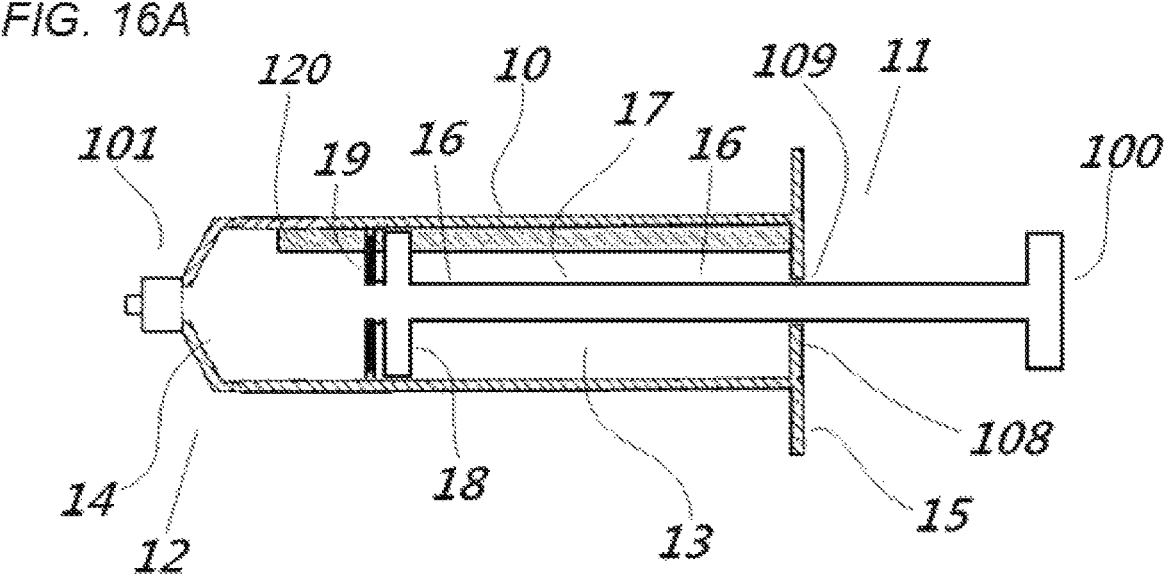
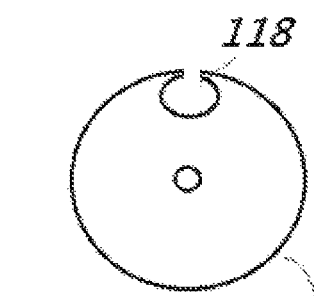
FIG. 16B
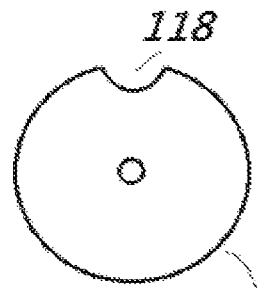
FIG. 16C
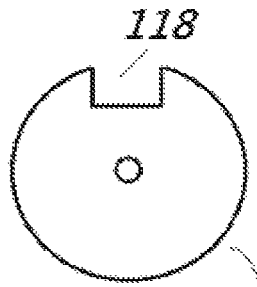
FIG. 16D

ERGONOMIC SUCTION SYRINGE AND METHODS OF USE

This application claims the benefit and priority date of U.S. Provisional Patent Application No. 62/815,067, EFS ID 35355265, and confirmation number 4909, filed Mar. 7, 2019, and titled "Ergonomic Suction Syringe and Methods of Use", and also claims the benefit and priority date of U.S. Provisional Patent Application No. 62/889,590, EFS ID 36932741, confirmation number 8285, filed Aug. 21, 2019, and titled "Ergonomic Suction Syringe and Methods of Use". Both provisional patent applications are incorporated herein in their entirety.

BACKGROUND

The following materials have been identified as potentially being informative for background purposes, and are incorporated herein in their entirety:

| Issued Pat. | Date Issued | Inventor |
| --- | --- | --- |
| U.S. 3,566,859 | Mar. 2, 1971 | Boris Schwartz |
| U.S. 3,747,812 | Jul. 24, 1973 | Harvey Karman |
| US38772864 | Mar. 25, 1975 | Robert E. Allen |
| U.S. 4,312,344 | Jan. 26, 1982 | Nils B. Nilson |
| U.S. 4,766,908 | Aug. 30, 1988 | Thomas P. Clement |
| U.S. 4,861,335 | Aug. 29, 1989 | David L. Reynolds |
| U.S. 5,176,642 | Jan. 5, 1993 | Thomas P. Clement |
| U.S. 5,354,285 | Oct. 11, 1994 | Sergej M. Mazurik |
| U.S. 5,549,573 | Aug. 27, 1996 | Wilhelm Waskonig |
| U.S. 5,891,052 | Apr. 6, 1999 | PaulL. Simmons |
| U.S. 6,245,046 | Jun. 12, 2001 | Wilmer L. Sibbitt |
| U.S. 7,806,858 | Oct. 5, 2010 | Jeffrey Smith |
| U.S. 8,088,104 | Jan. 3, 2012 | Jeffrey Smith |
| U.S. 9,101,713 | Aug. 11, 2015 | Kevin P. Cowan |

| Patent Application Number | Publication DateInventor |
| --- | --- |
| US20050192543A1 | Sep. 1, 2005 Wilmer Sibbitt |
| US20070032743A1 | Feb. 8, 2007 John A. Hibner |
| US20100324484A1 | Dec. 23, 2010 Jeffrey Smith |
| US20130126559A1 | May 23, 2013 Kevin P. Cowan |
| US20160151570A1 | Jun. 2, 2016 Edward J. Rhinehart |
| US20190029657A1 | Jan. 31, 2019 Morten Gulev |

Non-Patent Literature Documents

Randy R. Sibbitt, Wilmer L. Sibbitt, Jr, Sharon E. Nunez, Lawrence G. Kettwich, Sharon C. Kettwich, and Arthur D. Bankhurst. Control and Performance Characteristics of Eight Different Suction Biopsy Devices. J Vasc Intery Radiol 2006; 17:1657-1669.

Christopher J. Foster, Robert J. Teskey, Catherine M. Kells, Blair J. O'Neill, Nancy Fitzgeralld, Kim Foshar, Cathy Peck. Does the speed of balloon deflation affect the complication of coronary angioplasty? Am J Cardiol 1994; 73(4):228-30.

Alberts MB1, Shalit M, LoGalbo F. Ann Emerg Med. 2004 February; 43(2):181-6. Suction for venomous snakebite: a study of "mock venom" extraction in a human model.

Medical procedures that require removal of large volumes of fluid or gas often use "wall" suction, i.e., suction provided centrally within a medical facility and piped to points of care there through, with adapters that allow connecting hose and suction apparatuses to apply suction as needed for such applications. However, there are many applications in medicine where smaller volumes of gas, fluid, or tissue are removed assisted by manual suction for which manual dexterity is required, such as for example, obtaining needle biopsy of tissue, or deflation of angioplasty balloons, for which suction is traditionally applied using syringes attached to medical devices such as needles or catheters.

As an example, there are approximately 1.6 million breast needle biopsies and 600,000 thyroid needle biopsies done in the U.S. each year alone, with the world wide annual volume of needle biopsies estimated at 5 million. Needle biopsies can be done with automated cutting needles, like the commercially available Temno or Biopty needles, or with needle biopsy, either using fine needle aspiration (FNA) or manual coring needles (e.g., Franseen biopsy needle, Chiba biopsy needle). For either FNA or manual cutting needle biopsy, one method to obtain tissue is to perform an imaging test, often either ultrasound or computed tomography, based on the images plan a skin entry site for a biopsy needle, then usually under real time medical imaging guidance the needle is advanced into the tissue to be biopsied. Once appropriate position of the tip of the needle is confirmed, the stylet is removed from the needle (if present), suction is applied to the needle in an effort to draw tissue to be sampled into the needle lumen. Once this is achieved, the needle is often rotated and advanced and retracted over a few millimeters, and then the needle removed from the body, and the tissue sample expressed from the needle lumen or from the syringe, as needed. Tissue samples are then sent to a pathologist for analysis.

Worldwide, there are more than 7 million balloon angioplasty procedures done annually, and furthermore, angioplasty balloon catheters are often used in organs other than blood vessels, for example to dilate soft tissue tracts to permit percutaneous nephrolithotomy, passage of drainage tubes, placement of feeding tubes percutaneously, and to allow stents or tubes to be placed to bypass obstructions caused by tumors, for example in the biliary system. In addition to plain balloon angioplasty, angioplasty balloons are used often for deployment of vascular stents, for delivery of antiproliferative medications at sites of vascular interventions, during placement of endografts for aortic aneurysms, and for delivery of aortic valve prostheses percutaneously, among others.

Percutaneous balloon angioplasty is done using angioplasty balloon catheters. Angioplasty balloon catheters comprise a catheter with a balloon mounted toward a distal end. Said balloon is inflated during operation to treat a stenotic lesion, and then deflated and removed from the body. A typical angioplasty balloon catheter used in the peripheral circulation has an overall length of approximately 40-150 cm, with the length of the balloon approximately 2-20 cm, depending on the length of a stenosis being treated. Once appropriately positioned within the body, angioplasty balloons can be inflated by connecting a syringe or inflation device to the balloon lumen hub adapter, and then pressurizing fluid or gas in the chamber of the syringe or inflation device usually by manually depressing or advancing a piston in a cylinder of said syringe or of said inflation device. Angioplasty balloons, once fully inflated, do not need to stay inflated long. In order to deflate the angioplasty balloon, an operator applies suction to the angioplasty balloon lumen.

The usual method of creating suction manually for many medical procedures is to use a syringe, with the piston in the syringe placed fully into the cylindrical bore, then connecting said syringe to an adapter of the system requiring suction, then retracting the piston out of the cylinder to create suction. Using commonly available syringes, creating suction using a syringe is a two-hand operation, because the syringe body cylinder and the syringe need to be retracted in opposite directions. The disadvantage of conventional syringes when used to create suction is that they are not ergonomic, and for example maintaining suction on a needle during manipulation to obtain the tissue specimen is difficult, because in order to maintain suction two hands are required to distract the piston out the back of the syringe, leaving no free hand to perform rotation and advancement-retraction of the needle. Often an operator will attempt to manually "lock" the piston in its distracted position using one hand, but this is clumsy and doesn't afford optimal manual control of the needle.

There is a significant disadvantage to the current method of syringe deflation of angioplasty balloons, namely, that an operator must retract the piston out of the cylinder usually with two hands, and hold it as far out as possible with maximum manual force. This traction motion of the piston relative to the cylinder is not ergonomic. It often takes angioplasty balloons 20 or more seconds to fully deflate to the degree that they can be safely removed from the body. So, angioplasty balloon deflation is slow, laborious, and not ergonomic for the operator. Furthermore, slow balloon deflation times are associated with worse outcomes after coronary artery angioplasty (Christopher J. Foster, Robert J. Teskey, Catherine M. Kells, Blair J. O'Neill, Nancy Fitzgerald, Kim Foshar, Cathy Peck. Does the speed of balloon deflation affect the complication of coronary angioplasty? Am J Cardiol 1994; 73(4):228-30), so a way to apply ergonomically high-pressure suction using a single-hand device that, once actuated, maintains suction without other manipulation until the operator releases it would be a major advance and adjunct to the balloon angioplasty procedure.

There are several disadvantages of current manual suction devices and methods for obtaining manual suction on medical devices to perform medical procedures as done at present, such as:

(a) Creating suction with a conventional syringe is a bimanual, or two-hand, maneuver, leaving no hand free for operation of the medical device.
(b) The need to actively maintain suction throughout a medical procedure hinders facile manipulation of a medical device.
(c) Current manual suction devices cannot maintain suction hands-free, and require continual force to be applied to maintain suction.
(d) To create suction with a conventional syringe requires a pulling motion between the piston and the cylinder, i.e., they are retracted apart rather than compressed together, said pulling movement being more difficult to achieve than a pushing motion because of the relative strength of the involved muscle groups in humans.
(e) To achieve high negative pressures, i.e., suction, a large conventional syringe is typically used, for example 20-60 ml, which is bulky and reduces fine control of the attached medical device.
(f) Applying continued bimanual force on a large syringe, for example more than 15 seconds to evacuate an angioplasty balloon, requires considerable strength and can result in muscle and operator fatigue.
(g) Angioplasty balloon inflation devices are poorly designed to create suction because of their relatively small cylinder size and because often a large part or most of said cylinder is filled with fluid to perform balloon inflation, further reducing the chamber size for achieving the suction.
(h) Relatively slow angioplasty balloon deflation times can result in adverse events and patient injury compared to more rapid angioplasty balloon deflation times.

SUMMARY

The disclosure herein is a hand-held medical device that comprises an ergonomic suction syringe that can generate substantial suction to be transmitted to other medical devices such as biopsy needles or angioplasty balloons with ergonomic one-handed operation by forward motion of a piston into a cylinder of a syringe. In one embodiment, the invention is an ergonomic suction syringe, the operation being generally reversed compared to a conventional syringe because when a piston is advanced forward into the cylinder negative pressure is transmitted to an adapter tip instead of positive pressure, and by extension said negative pressure is transmitted to an attached medical device. Thus, the ergonomic suction syringe works opposite of a conventional syringe, i.e., when the piston is moved in a forward direction into a cylinder, suction is generated in an attached medical device rather than pressure. An ergonomic suction syringe comprises a hollow cylinder within which a piston is slidably contained, and has a back end generally disposed toward an operator, said back end including a mechanism for manipulation of a piston, and a forward end generally disposed toward a medical device that includes an adapter tip, said adapter tip allowing connection to another medical device, for example a needle or catheter, for example by means of a Luer lock connection, said medical device generally comprising a hollow lumen. An ergonomic suction syringe has a cylinder that has two generally air-tight chambers, comprising a back chamber disposed toward said back end and a forward chamber disposed toward said forward end, said back chamber and said forward chamber being separated by a piston head, said piston head occupying essentially the entire cross-sectional area of an interior of said cylinder, said piston head comprising a sealable but slidable interface with an inner wall of said cylinder, and said piston head mounted on a forward end of a piston rod, said rod occupying less than essentially the entire-cross sectional area of the interior of said cylinder, said piston head functioning generally as a diaphragm between said back chamber and said forward chamber. Unlike many conventional syringes, said back chamber is not open to the atmosphere at its back end, but is sealed off by a membrane, said membrane having an aperture through which said piston rod moves slidably, but comprising an air-tight seal to said piston rod. When said piston is advanced into said cylinder, suction is generated in said back chamber. As said piston is advanced slidably forward within said cylinder, vacuum pressure increases in said back chamber. Said ergonomic suction syringe comprises a means to transmit said vacuum pressure from said back chamber to said forward chamber. In one embodiment, said means to transmit vacuum to said forward chamber is deformation of a gasket adherent to said piston head, said gasket having a first configuration, said gasket deforming to a second configuration after a critical threshold of vacuum in said back chamber is achieved, said critical threshold actuating said gasket, thereby resulting in a change in said gasket's physical shape, thereby permitting escape of gas from said forward chamber to said back chamber, accompanied by transmission of said suction pressure from said back chamber to said forward chamber, and by extension to a hollow lumen of said attached medical device. In one embodiment, a means to allow gas exchange between said forward chamber and said back chamber is a shape or configuration of said piston head, and in another embodiment said means to allow gas exchange between said forward chamber and said back chamber is a mechanical apparatus, e.g., a valve. In yet a third exemplary embodiment, said means of transmitting vacuum from said back chamber to said forward chamber is a perforation in said piston rod or in said piston head, said perforation not communicating with said forward chamber until said piston rod is advanced to a preferred location in said forward chamber, whereupon when said perforation is positioned at said preferred location said perforation creates a window between said back chamber and said forward chamber. In another variation of said third exemplary embodiment, said window between said back chamber and said forward chamber is created by having an inner cylinder tube element that is fixed in position relative to said cylinder, is slidably inserted within said piston rod, said lumen of said inner cylinder tube being sealed toward the back chamber but having at least a perforation in its forward end, said perforation being capable of aligning with said perforation in said piston rod when said piston rod is advanced to a preferred position forward within said cylinder. Said inner cylinder tube may also have at least a second perforation located forward of said piston rod perforation to allow gas or liquid in said forward chamber to be expelled from the tip of said ergonomic suction syringe when said piston rod is advanced in said cylinder, said advancement thereby pressurizing said gas or said liquid.

In an exemplary embodiment, when said vacuum is transmitted to the tip of said ergonomic suction syringe, said vacuum would remain without requiring continued application of force for as long as the operator desires, generally permanently, without any manual contact whatsoever, that is, hands-free for example when used for deflation of angioplasty balloons or tissue biopsy. However, retraction of the plunger out of said back end of said cylinder has a means to cause a loss of seal between said forward chamber and said back chamber, thereby releasing suction applied at said adapter tip and by extension any medical device attached thereto. Further, if the ergonomic suction syringe is connected to a needle, or to the hub of an angioplasty balloon lumen of an angioplasty balloon, suction applied to said needle and to said angioplasty balloon lumen would persist until either the ergonomic suction syringe is disconnected from said needle or said angioplasty balloon lumen or until said piston is retracted. Such an ergonomic suction syringe permits single-hand actuation of suction for procedures where fine motor control is useful, like during fine needle aspiration, further assisted by the ability to set suction by a forward, one-handed, slidable movement of the piston within the syringe cylinder, and then retention of suction for the duration of the medical procedure hands-free without any further effort by an operator.

An ergonomic suction syringe significantly facilitates deflation of angioplasty balloons compared to conventional syringes, because angioplasty balloons often deflate slowly, 17 seconds or more, which is a long time to maintain bimanual traction on a syringe. For example, an angioplasty procedure could consist of an operator inflating an angioplasty balloon with a dedicated inflator or a conventional syringe, and when satisfied that the angioplasty has been completed, said operator removing said conventional syringe or balloon inflator and attaching an ergonomic suction syringe by slidably moving said plunger forward with one hand using a thumb to advance said piston and two fingers used to control the cylinder, causing the piston to advance into the cylinder, and once suction is actuated to an attached angioplasty balloon lumen the operator no longer needs to continue to apply any force, or even to hold the ergonomic suction syringe, while the angioplasty balloon deflates.

In one exemplary embodiment, a forward chamber of an ergonomic suction syringe has a one-way check valve that permits movement of pressurized gas or liquid from the forward chamber to an atmosphere when a piston is slidably moved forward within a cylinder when an adapter tip of said ergonomic suction syringe is connected to a closed-system medical device, for example, to a lumen of an inflated angioplasty balloon, said one-way check valve serving to preserve suction by closing of said one-way check valve to prevent inflow of gas from said atmosphere into said forward chamber when suction is transmitted into said forward chamber. Said one-way check valve could be integral to the cylinder or a removable component, can be located toward a forward aspect of the cylinder, on said adapter tip, or an external component attached to said adapter tip. Said ergonomic suction syringe could be incorporated into an inflation device as an integral component of it, or be a component and assembled along with an inflation device as a modular device for use for example to inflate and to deflate angioplasty balloons through a common connection to said angioplasty balloon.

An exemplary method of operation of an ergonomic suction syringe for imparting suction to an attached medical device comprises:

(a) attaching said ergonomic suction syringe comprising a back end generally disposed toward an operator and a front end generally disposed toward a medical device during use, said ergonomic suction syringe comprising a cylinder including at least two generally air-tight chambers, including at least a back chamber disposed toward said back end and a forward chamber disposed toward said forward end, said forward chamber and said back chamber being separated by a piston head, said piston head mounted to a piston rod, said back chamber having a means to prevent loss of suction through said back chamber back end, said piston head occupying essentially the entire cross-sectional area of the interior of the cylinder, said piston head or said piston rod comprising a means for transmission of vacuum from said back chamber to said front chamber, said piston head also comprising a means to further seal said piston head outer diameter to an inner diameter of said cylinder, except in one exemplary embodiment when a critical threshold of suction pressure in said back chamber is exceeded, said piston head functioning essentially as a diaphragm between said two chambers, and said piston head mounted on the forward end of said piston rod, said piston rod occupying less than essentially the entire-cross sectional area of the interior of the cylinder, securely to a medical device, for example, a needle, a suction tube such as for example a Yankauer tip, an angioplasty balloon lumen, and a catheter, by means of an adapter tip, for example, a Luer lock connection. In one exemplary embodiment, means of transmitting vacuum from said back chamber to said forward chamber is a perforation in said piston rod or in said piston head, said perforation not communicating with said forward chamber until said piston rod is advanced to a preferred location in said forward chamber, whereupon when said perforation is positioned at said preferred location said perforation creates a window between said back chamber and said forward chamber. In another variation of said third exemplary embodiment, said window between said back chamber and said forward chamber is created by having an inner cylinder tube element that is fixed in position relative to said cylinder, is slidably inserted within said piston rod, said lumen of said inner cylinder tube being sealed toward the back chamber but having at least a perforation in its forward end, said perforation being capable of aligning with said perforation in said piston rod when said piston rod is advanced to a preferred position forward within said cylinder. Said inner cylinder tube may also have at least a second perforation located forward of said piston rod perforation to allow gas or liquid in said forward chamber to be expelled from the tip of said ergonomic suction syringe when said piston rod is advanced in said cylinder, said advancement thereby pressurizing said gas or said liquid.

(b) actuating suction in the forward chamber by slidably advancing said piston in a forward direction within said chamber, compressed gas in said forward chamber escaping through said one-way valve, said piston advanced until a means of transmitting vacuum from said back chamber to said forward chamber is achieved, thereby allowing vacuum to be transmitted by extension to an attached medical device.

For example, an angioplasty procedure could consist of an operator inflating an angioplasty balloon with a dedicated inflator or a conventional syringe, and when satisfied that the angioplasty has been completed, removing said dedicated inflator or conventional syringe and attaching an ergonomic suction syringe, then advancing a piston in said ergonomic suction syringe while maintaining a cylinder of said ergonomic suction syringe in stable position relative to said piston using one hand, said suction being transmitted to an attached medical device. Once suction is applied the operator no longer needs to continue to apply any force, or even to hold the ergonomic suction syringe, to maintain vacuum in said attached medical device. As another example of evacuating an angioplasty balloon, both said dedicated inflation device or conventional syringe and said ergonomic suction syringe could be connected through a mutual connector to said angioplasty balloon lumen. Other exemplary medical applications for an ergonomic suction syringe include: blood vessel needle access, joint aspiration, spinal fluid aspiration, abscess drainage, kidney needle access, biliary needle access, gall bladder needle access, surgical wound drainage, and medication reconstitution.

Advantages of an ergonomic suction syringe:

(a) Creating suction with an ergonomic suction syringe can be done with one hand, leaving the other hand for other tasks, for example, for performance of a tissue biopsy.

(b) Once suction is achieve in a lumen of said medical device, no further effort is required by the operator to maintain suction essentially permanently, and said suction can even be maintained hands-free of the ergonomic suction syringe, hands-free.

(c) Creation of suction with an ergonomic suction syringe is done with ergonomic compression motion of the piston relative to the cylinder, which is mechanically advantageous compared to pulling.

(d) Creating suction with one hand facilitates performance of medical procedures, enabling fine-motor control of medical devices, for example, biopsy needles (e) Applying single-hand forward motion of the piston into the cylinder to achieve suction in the forward chamber and thereby in any attached medical device is ergonomic easy and fast, requiring only a second or two of force, thereby mitigating the chance of muscle fatigue.

BRIEF DESCRIPTION

Figure 6A:
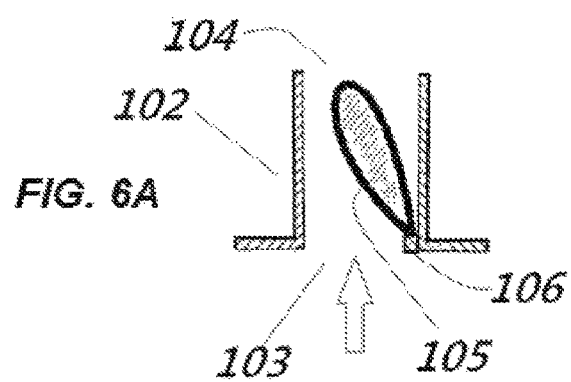
Figure 6B:
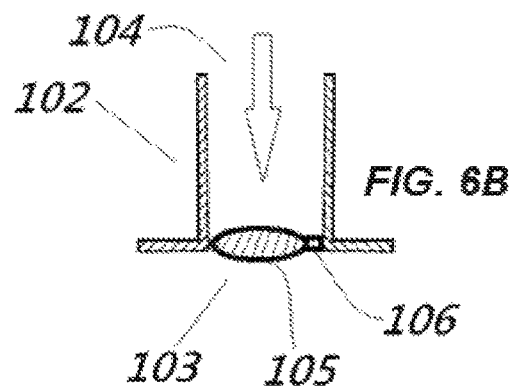
Figure 6C:
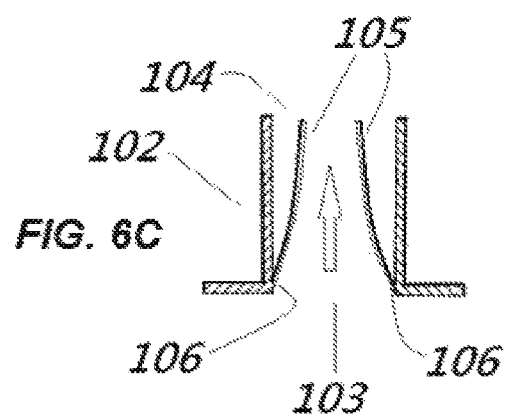
Figure 6D:
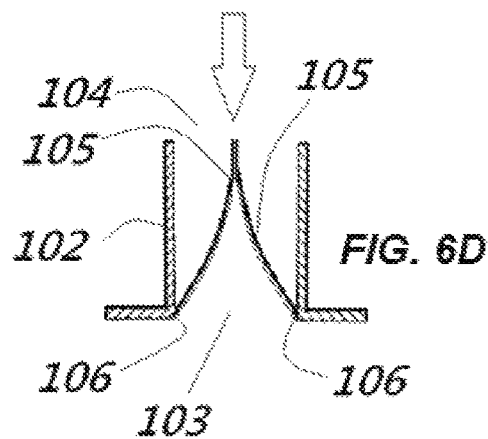

FIG. 6A is a cut-away view of a component of an exemplary embodiment of an ergonomic suction syringe comprising a one-way valve. FIG. 6B is a cut-away view of a component of another exemplary embodiment of an ergonomic suction syringe comprising a one-way valve. FIG. 6C is a cut-away view of a component of another exemplary embodiment of an ergonomic suction syringe comprising a one-way valve. FIG. 6D is a cut-away view of a component of another exemplary embodiment of an ergonomic suction syringe comprising a one-way valve.

FIG. 7 is a surface view of a lateral aspect of an exemplary embodiment of an ergonomic suction syringe.

Figure 8:
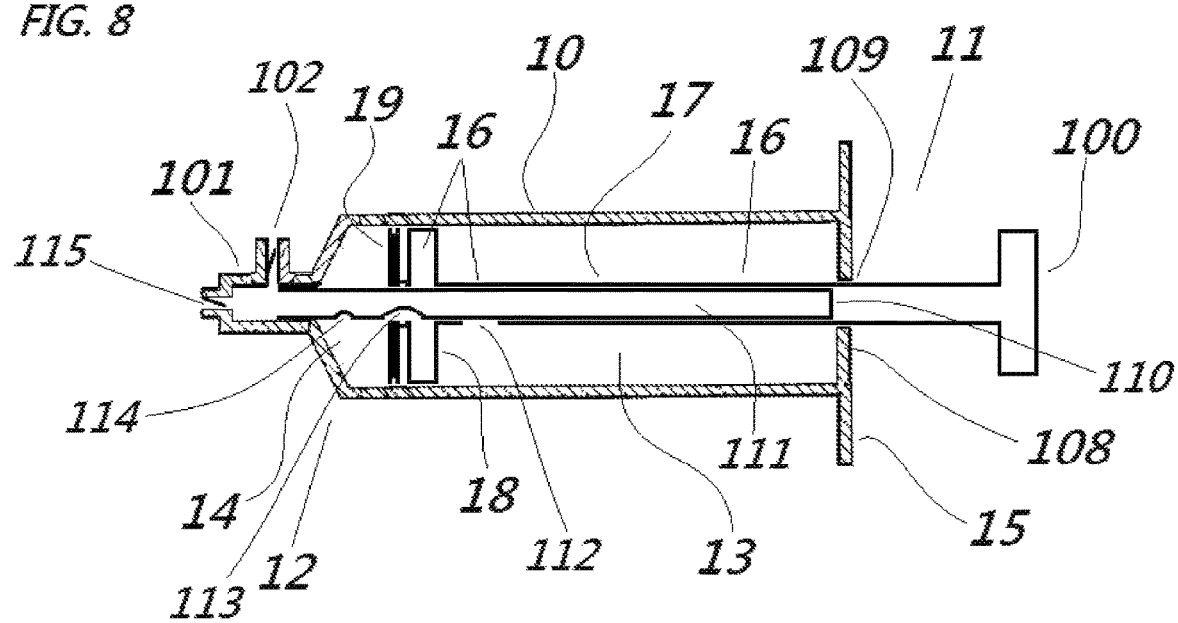

FIG. 8 is a cut-away longitudinal view of another exemplary embodiment of an ergonomic suction syringe, in this illustration with the piston head in a forward position but vacuum not transmitted to the tip adapter of the ergonomic suction syringe.

Figure 9:
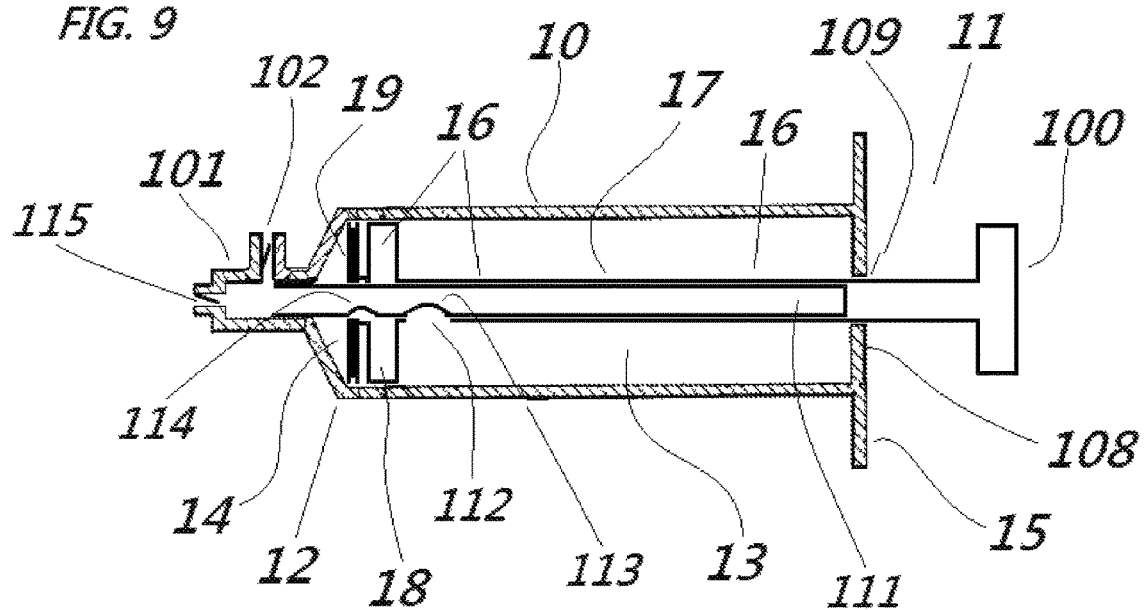

FIG. 9 is a cut-away longitudinal view of a similar exemplary embodiment of an ergonomic suction syringe of FIG. 8, in this illustration with the piston head in a forward position in alignment such that vacuum is transmitted to the tip adapter of the ergonomic suction syringe.

Figure 10A:
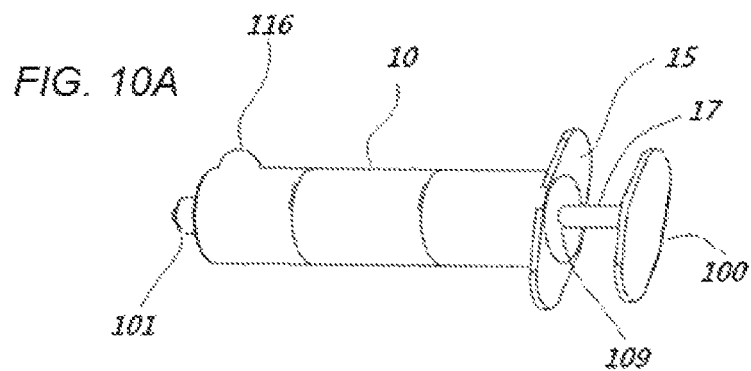
Figure 10B:
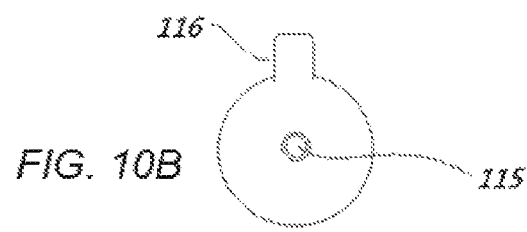

FIG. 10A is an oblique surface view of an exemplary embodiment of an ergonomic suction syringe, and FIG. 10B is an end-on surface view of the same embodiment of an ergonomic suction syringe from the distal tip end.

Figure 11A:
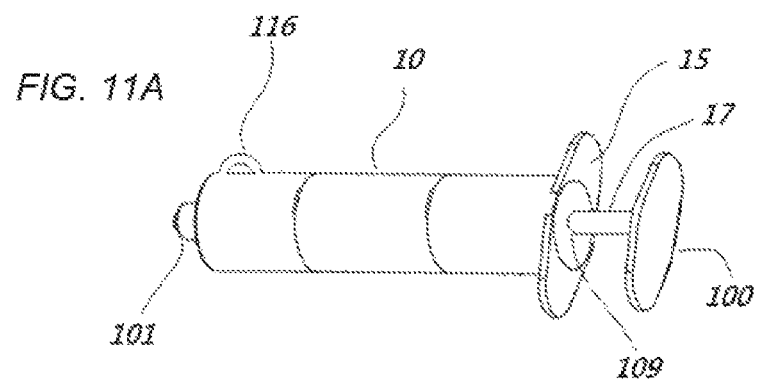
Figure 11B:
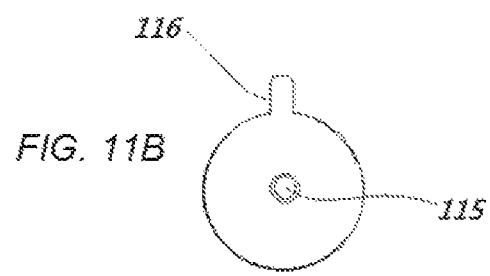

FIG. 11A is an oblique surface view of another exemplary embodiment of an ergonomic suction syringe, and FIG. 11B is an end-on surface view of the same embodiment of an ergonomic suction syringe from the distal tip end.

Figure 12:
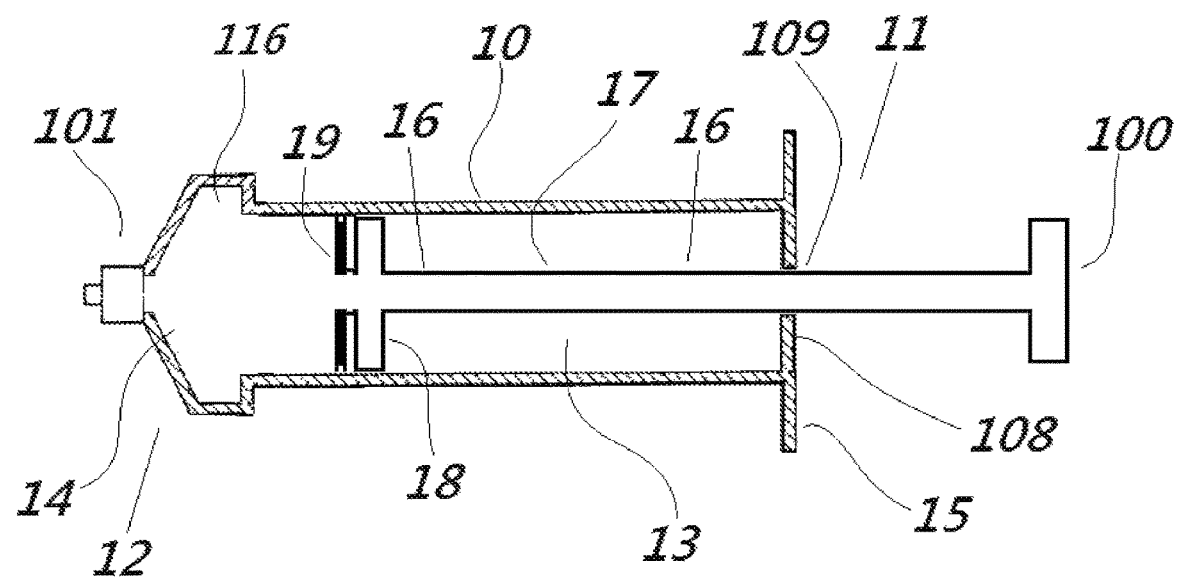

FIG. 12 is a cut-away longitudinal view of another exemplary embodiment of an ergonomic suction syringe.

Figure 13:
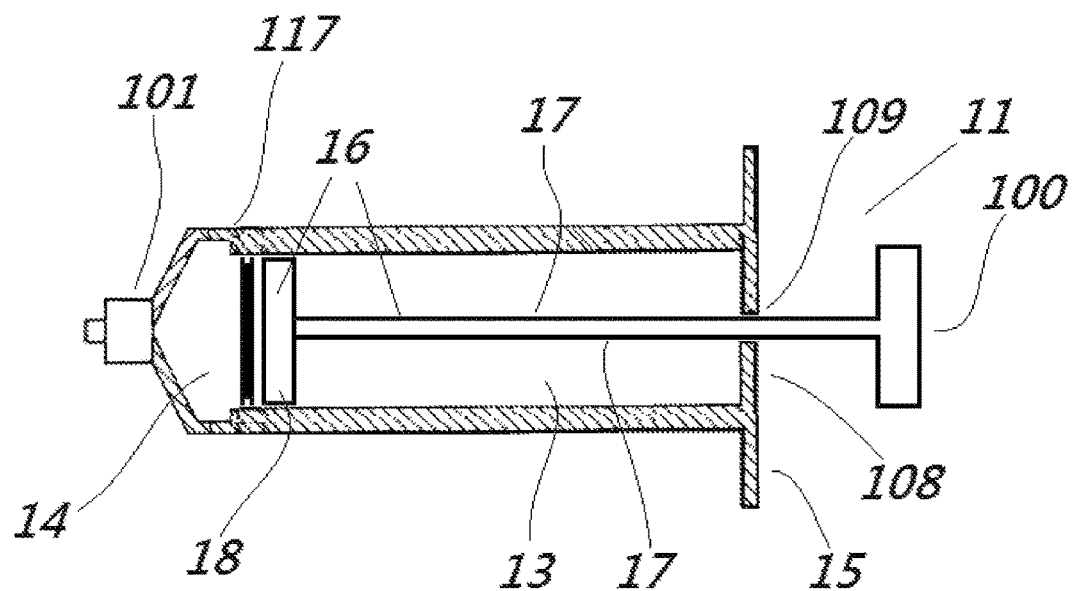

FIG. 13 is a cut-away longitudinal view of another exemplary embodiment of an ergonomic suction syringe.

Figure 14A:
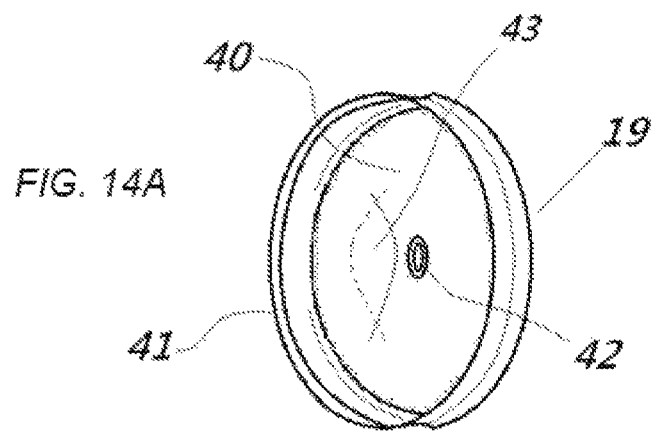
Figure 14B:
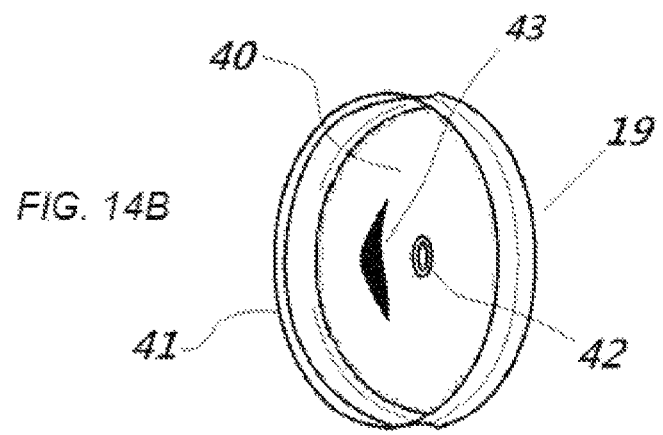

FIG. 14A is an oblique surface view of an exemplary embodiment of a piston head gasket. FIG. 14B is an oblique surface view of another configuration of an exemplary embodiment of a piston head gasket.

Figure 15A:
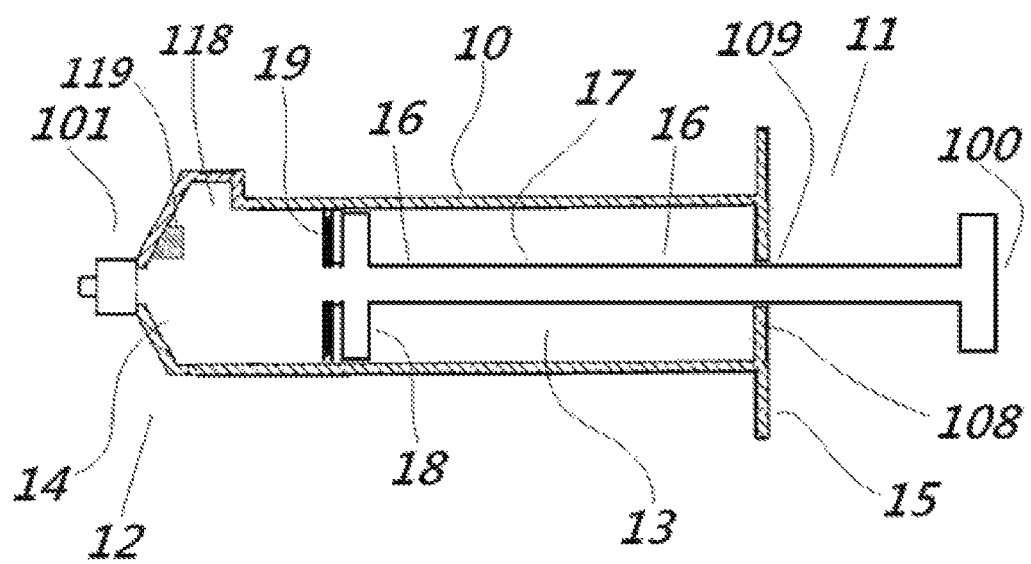
Figure 15B:
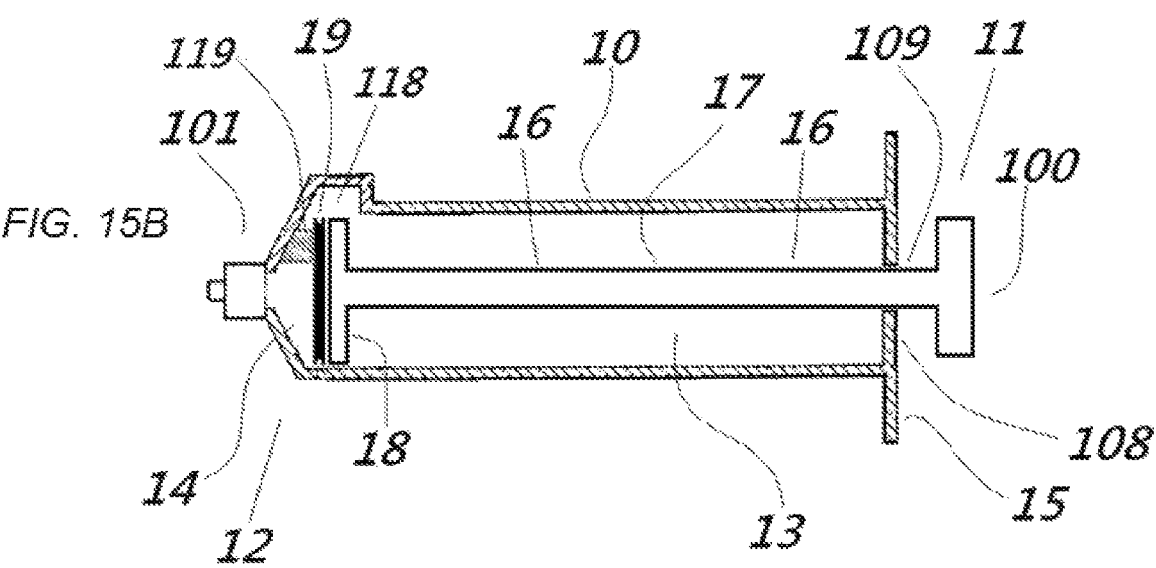

FIG. 15A is a cut-away longitudinal view of an exemplary embodiment of an ergonomic suction syringe in configuration where the vacuum is not transmitted to an adapter at the distal tip of said ergonomic suction syringe. FIG. 15B is a cut-away longitudinal view of an exemplary embodiment of an ergonomic suction syringe in configuration where the vacuum is transmitted to an adapter at the distal tip of said ergonomic suction syringe.

FIG. 16A is a cut-away longitudinal view of an exemplary embodiment of an ergonomic suction syringe in configuration where the vacuum is not transmitted to an adapter at the distal tip of said ergonomic suction syringe. FIG. 16B is an en face view of an exemplary embodiment of a piston head configuration. FIG. 16C is an en face view of another exemplary embodiment of a piston head configuration. FIG.

16D is an en face view of yet another exemplary embodiment of a piston head configuration.

Figure 17A:
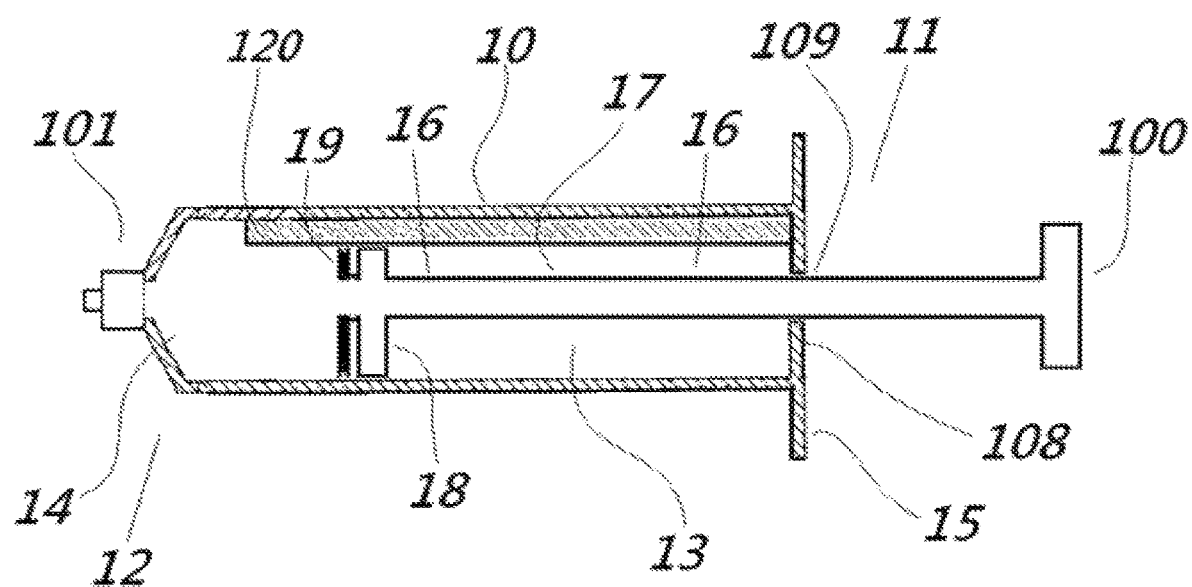
Figure 17B:
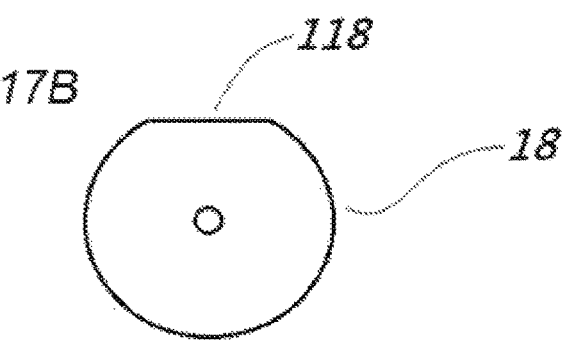

FIG. 17A is a cut-away longitudinal view of an exemplary embodiment of an ergonomic suction syringe in configuration where the vacuum is not transmitted to an adapter at the distal tip of said ergonomic suction syringe. FIG. 17B is an en face view of an exemplary embodiment of a piston head configuration.

DETAILED DESCRIPTION OF THE DRAWINGS

Figure 1:
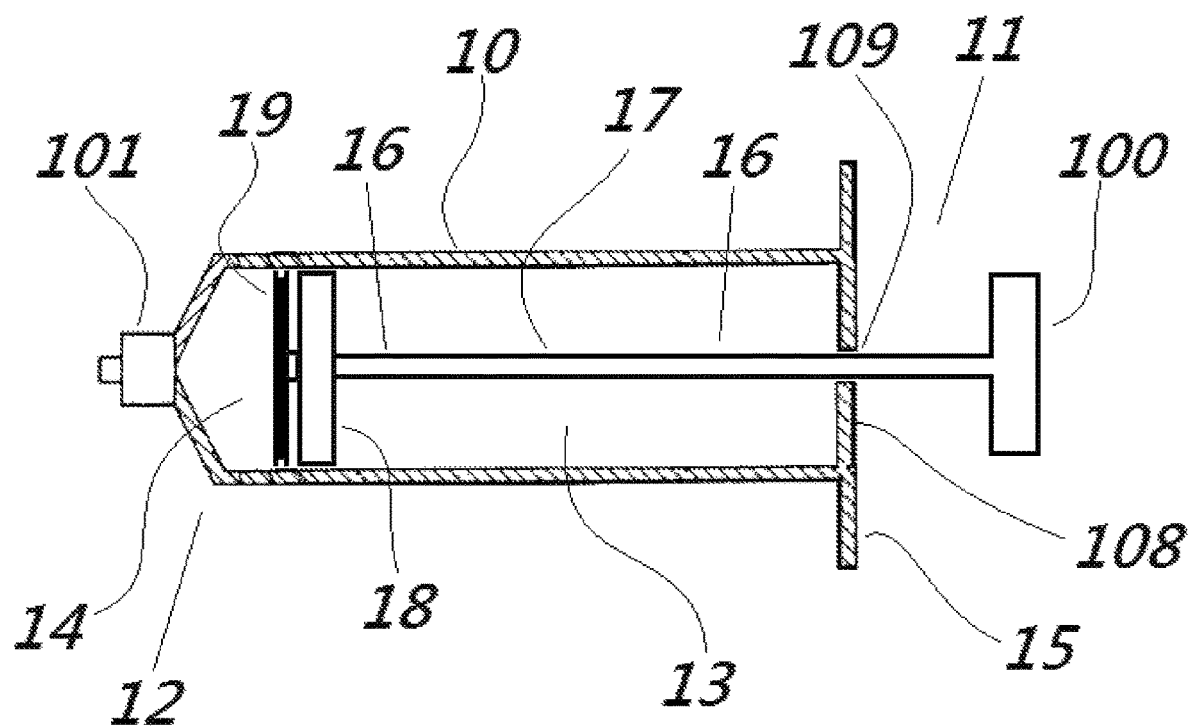
FIG. 1 is a cut-away longitudinal view of an exemplary embodiment of an ergonomic suction syringe.

An ergonomic suction syringe as disclosed herein is designed to create suction in an attached medical device when a piston is advanced into a syringe cylinder, rather than pressure, and as such, will transmit suction to an attached medical device, rather than injecting pressurized fluids or gases. From FIG. 1, an exemplary embodiment of an ergonomic suction syringe comprises a cylinder 10 and a piston 16, said piston comprising a piston rod 17 and a piston head 18, said ergonomic suction syringe including a back end 11 generally disposed toward an operator during use, and a forward end 12 generally disposed toward a medical device during use, said forward end 12 including a tip adapter 101 that allows the ergonomic suction syringe to be connected reversibly to other medical equipment, for example, a needle and a catheter, in some embodiments by a Luer lock connection, and also is a means of egress from a forward chamber 14 for transmission of fluids, gases, or liquids therethrough. Said ergonomic suction syringe includes a back chamber 13, said back chamber 13 closed to said atmosphere by a diaphragm 108, said diaphragm 108 having an aperture whereby said piston rod 17 can move slidably there through, said piston 16 having a piston rod 17 and said aperture 109 having a first generally air-tight seal, said ergonomic suction syringe in which negative pressure is generated in said back chamber 13 by forward sliding motion of a piston head 18 relative to said cylinder, said piston head 18 oriented generally perpendicular to the long axis of said cylinder 10, said piston head 18 generally separating said cylinder 10 into said back chamber 13 and said forward chamber 14, movement in a forward direction of said piston 16 actuated for example by force applied to a piston tab 100 while simultaneously constraining forward motion of the cylinder 10, which the operator may perform for example by holding the cylinder 10 or by manually controlling tabs 15, for example by a one-hand maneuver, said forward advancement of said piston head 18 transmitted by said piston rod 17. In this example, a second air-tight seal between said forward chamber 14 and said back chamber 13 comprises a gasket 19 affixed to the piston head 18, or in other embodiments, a gasket affixed around the circumference of said piston head 18.

Figure 2:
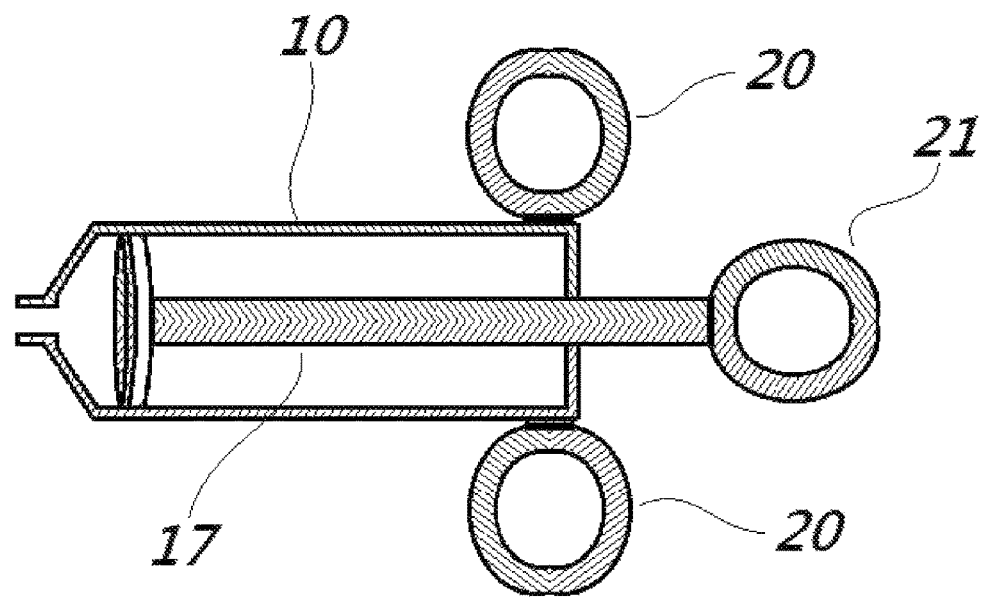
FIG. 2 is another cut-away longitudinal view of an exemplary embodiment of a reverse operation syringe, in this view with finger rings as a means for manipulation of said reverse operation syringe.

FIG. 2 is another exemplary embodiment of a reverse operation syringe, in this example illustrating an ergonomic suction syringe with a plurality of ring tabs 20 on at least said cylinder and at least another ring tab on said piston 21.

Figure 3:
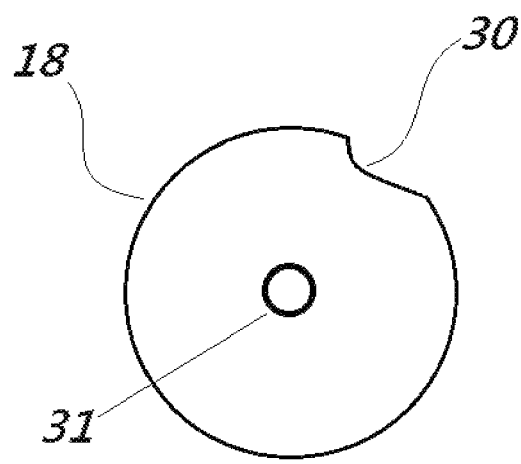
FIG. 3 is an end-on view of an example of a component of an ergonomic suction syringe, comprising a piston head.

FIG. 3 is an illustration of an exemplary embodiment of a piston head 18, comprising a structure that is generally circular in one aspect, but in general is shaped like a short cylinder or a disk in that said piston head presents an essentially circular shape when viewed en face but presents an essentially rectangular shape when viewed from a side. In one example, the piston head 18 is not a perfect circle when viewed enface but contains a notch 30 in its outer edge, said notch permitting vacuum to pass from said back chamber 13 to said forward chamber 14 during operation of the ergonomic suction syringe when a threshold back chamber suction pressure is achieved, thereby transmitting suction from said back chamber 13 to said forward chamber 14, and, by extension, to a medical device, said medical device comprising a closed system without communication to the atmosphere, to said forward chamber 14 by securely affixing said medical device to an adapter tip 101. This example is provided to illustrate one design of a defect in said piston head 18 that could provide a means of transmission of vacuum from said back chamber to said forward chamber once a critical threshold of vacuum is exceeded and a change in configuration of said piston gasket 19 occurs, but one can readily appreciate that many other configurations of defects in said piston head could achieve the same function, such as for noncomprehensive example fenestrations, flap valves, trap doors, hinged segments. When attached to a closed system, suction will essentially remain until the piston is move back relative to the cylinder 10, whereupon the gasket will be deformed and not provide an airtight seal, and gas will move from the back chamber 13 into said forward chamber 14, relieving the suction in said forward chamber 14. An alternative means to relieve the pressure, among others, would be to disconnect the tip adapter 101 from said medical device, exposing the adapter tip 101 to said atmosphere. In this illustration there is a central receptacle 31 as a means for connecting said piston head 18 and said piston shaft 17, but in other examples they could be fabricated integral to each other.

Figure 4:
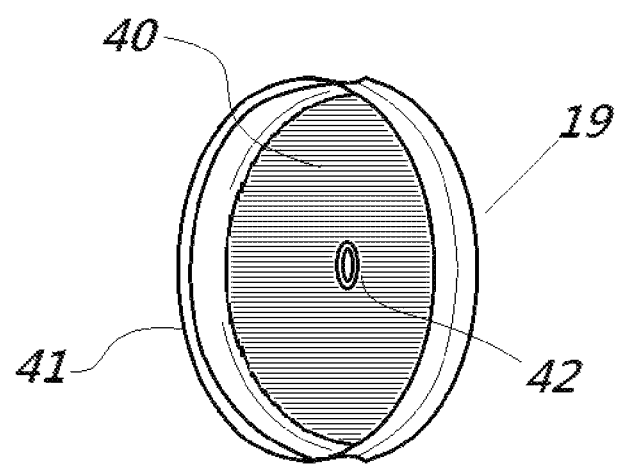
FIG. 4 is an oblique view of an example of a component of an ergonomic suction syringe, comprising a piston head gasket.

FIG. 4 is an illustration of an embodiment of a piston gasket 19, comprising a base 40 and a rim 41 generally perpendicular thereto. Said piston gasket 19 is generally round in one dimension and is in contact with an inner aspect of said cylinder 10, but not secured to it, so that when said piston is moved within said cylinder 10, said piston gasket 19 serves as a means to prevent movement of gas or liquid from said forward chamber 14 into said back chamber 13 until a critical threshold of suction pressure is achieved. When said critical threshold of suction pressure is achieved, said means to prevent movement of vacuum from said back chamber 13 into said forward chamber 14 fails, and suction is transmitted to said forward chamber and to a medical device attached thereto. In one embodiment, once suction is transmitted to said forward chamber and to a medical device attached thereto, the piston gasket 19 reverts to its original shape and again serves as a means of an air-tight seal between said forward chamber 14 and said back chamber 13. In another embodiment, once suction is transmitted to said forward chamber 13 and said piston gasket 19 transforms to its initial shape, it is incompetent to the movement of gases and fluids on retraction and allows free movement of gases and fluids that were accumulated in said back chamber 13 into said forward chamber 14. In another embodiment, said back chamber has other means for allowing ejection of gases or fluids therein, in one example for illustration only that doesn't limit this disclosure, said means of allowing ejection of gases or fluids from said back chamber may be a one valve located accordingly on said walls of said back chamber through which fluids or gases can pass unidirectionally out of said back chamber 13 with retraction of said piston rod 17 toward said back end 11 of said ergonomic suction syringe. In one embodiment said piston gasket 19 is securely attached to a forward aspect of said piston head 18, but in other embodiments said gasket 19 could be attached to an outer circumference of said piston head 18, or said gasket 19 could be attached to the back surface of the piston head 18, or said gasket 19 could be absent altogether, among other embodiments.

Figure 5A:
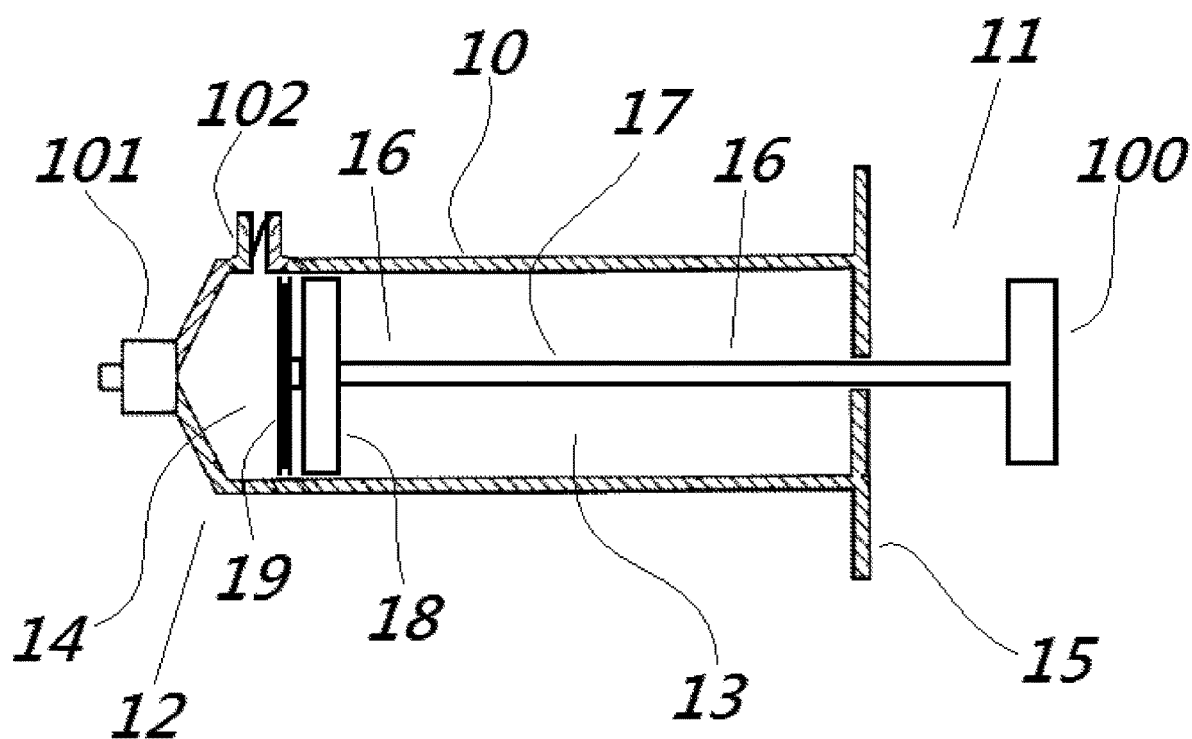
FIG. 5A is a cut-away longitudinal view of an exemplary embodiment of an ergonomic suction syringe.
Figure 5B:
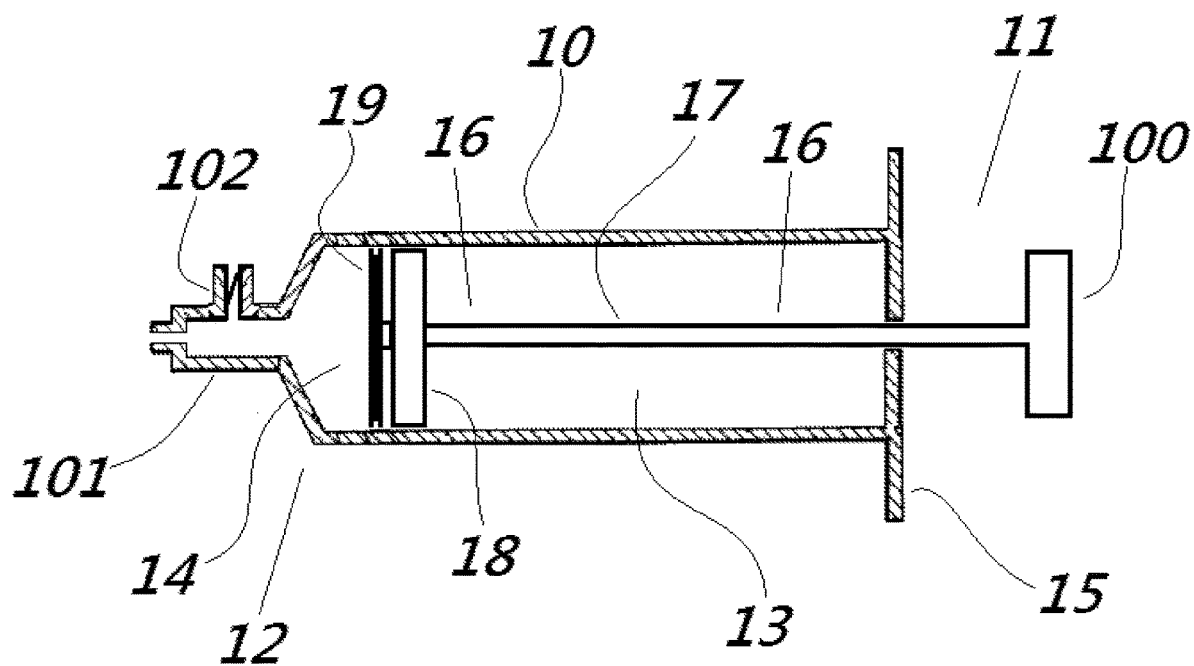
FIG. 5B is a cut-away longitudinal view of an exemplary embodiment of an ergonomic suction syringe.

In FIG. 5A another exemplary embodiment of an ergonomic suction syringe is illustrated, this example also including an exit port 102 for gases or fluids from said forward chamber 14, in this exemplary embodiment comprising a one-way valve such that fluid or gas can exit said forward chamber 14 but not enter said forward chamber 14, as the piston is slidably moved forward relative to the cylinder 10, in this example said one-way valve is securely attached to the side of the forward chamber 14. FIG. 5B illustrates another embodiment of said exit port 102, in this example securely attached to the side of a tip adapter 101. It can be readily envisioned by those familiar with the field that said exit port 102 could also be an external component and reversibly connected to said adapter tip 101.

FIG. 6A is an illustration of a magnified view of exemplary side ports 102 which in these examples comprise one-way valve, in this example comprising a flap valve, which comprises a closable valve element 105 and an attachment means 106 to one aspect of said one-way valve. In this illustration, the arrow is within said forward chamber 14, and shows the direction of motion of gas out of the cylinder 10 during forward motion of the piston 16 relative to the cylinder 10. Those familiar with the art will understand that during initial forward motion of the piston 16, gas will be expelled from said forward chamber 14 to said atmosphere. In one embodiment, when forward motion of said piston 16 continues until said critical threshold of suction is achieved and said gasket 19 fails to provide an air-tight seal, thereby permitting movement of gas from said forward chamber 14 to said back chamber 13 and transmission of suction from said back chamber 13 to said forward chamber 14, gas will be initially drawn into said forward chamber 13 in a direction indicated by the arrow, and said flap 105 will move to a closed position as shown in FIG. 6B, preventing gas from outside of said ergonomic suction syringe from entering said forward chamber 14, thereby preserving suction therein and by extension in an attached medical device. FIG. 6C is a cut-away magnified view of a similar one-way valve, comprising in this embodiment a duck-bill valve, shown in an open position for example during initial forward motion of said piston (arrow depicts direction of motion of gas from the forward chamber 14 to said atmosphere), and in FIG. 6D, after a critical threshold of suction pressure is achieved and said gasket 19 fails to provide air-tight seal, thereby permitting movement of gas from said forward chamber 14 to said back chamber 13 and transmission of suction from said back chamber 13 to said forward chamber 14, a closable member 105 will move to a closed position, thereby preventing loss of suction in said forward chamber 14 and any attached medical device.

FIG. 7 is another embodiment of an ergonomic suction syringe, in this example including a one-way valve comprising an aperture 107 in a sidewall of said cylinder 10 forward chamber (not shown) covered with a compliant band as a means to permit egress of gas from said forward chamber during forward motion of said piston 16 relative to said cylinder 10 while preventing ingress of gas from said atmosphere into said forward chamber 14 after a critical threshold of suction pressure is achieved and said gasket 19 fails to provide air-tight seal between said forward chamber 14 and said back chamber 13, whereby suction is transmitted from said back chamber 13 to said forward chamber 14.

FIG. 8 and FIG. 9 illustrate another exemplary embodiment of an ergonomic suction syringe shown in longitudinal sections, in which said piston 16 is advanced generally toward a forward end of a forward chamber 14, and in said configuration vacuum would be present in said back chamber 13 but not transmitted to said tip adapter 101 of said ergonomic suction syringe. In this embodiment said piston rod 17 comprises a hollow central lumen 111, and also comprises at least an aperture 112 as a means of egress that permits fluid and gas communication between an inner aspect and an outer aspect of said piston rod 17, said aperture 112 disposed generally toward a forward end of said piston rod 17. Further, in this exemplary embodiment of an ergonomic suction syringe there is an inner cylinder tube 110 that comprises a hollow central lumen, and that is air-tight securely mounted to a forward element of said cylinder 10, and over which said piston rod 17 is mounted thereon slideably but generally sealed to movement of liquid or gas between an outer aspect of said inner cylinder tube 110 and an inner aspect of said piston rod 17. Moreover, in this exemplary embodiment of an ergonomic suction syringe said inner cylinder tube 110 comprises at least an aperture 113 generally disposed toward a forward end of said inner cylinder tube 110 that permits fluid or gas communication between an inner aspect of said inner cylinder tube 110 and an outer aspect of said inner said cylinder tube 110, said outer aspect of said inner cylinder tube corresponding to an inner aspect of said piston rod 17 where said inner cylinder tube 110 and said outer piston rod 17 overlap. In some embodiments of said ergonomic suction syringe said inner cylinder tube 110 may also comprise at least another forward aperture 114 that serves as a communication between said forward chamber 14 and an inner lumen of said adapter tip 101, thereby by extension to an attached medical device (not shown). Said forward aperture 114 for example is located in a position such that it allows gas or liquid to pass from said forward cylinder chamber 14 during advancement of said piston 16 until said piston head 18 covers said forward aperture 114, thereby sealing further passage of fluid or gas across said forward aperture 114, and allowing vacuum to be transmitted to said adapter tip 101 without any loss of vacuum through said forward aperture 114. For example, a way of operating this embodiment of an ergonomic suction syringe is to connect said ergonomic suction syringe to a medical device at an adapter 101 generally disposed at a forward end of said cylinder 10, and to begin application of vacuum to said medical device by starting with said piston 16 fully retracted in a direction toward said back end 11 of said cylinder 10 such that said piston head 18 is generally disposed toward said back end of said back chamber 13, and then advancing said piston 17 forward in said cylinder 10, to a position generally depicted in FIG. 8, said advancing motion generating vacuum in said back chamber 13, and continuing to advance said piston 16 until said piston head 18 is generally disposed toward a forward end of said forward chamber 14, advancing said piston 16 until said piston rod aperture 112 generally aligns with said inner cylinder tube aperture 113 as generally depicted in FIG. 9, whereupon vacuum generated in said back chamber 113 is transmitted into said inner lumen 111 of said inner cylinder tube 110, and thereby to said attached medical device (not shown) via a lumen 115 of said adapter tip 101, said lumen 115 of said adapter tip in some embodiments also comprising a one-way valve that permits fluid or gas to enter said forward chamber 14 but not to exit said forward chamber 14. Further, said piston rod 16 or said inner cylinder tube 110 may comprise means of maintaining alignment of said piston rod aperture 112 and said inner cylinder tube aperture 113 such that when said piston rod 16 is advanced said piston rod aperture 112 interfaces directly with said inner cylinder tube aperture 113. In an exemplary embodiment, said advancing motion of said piston 17 in said cylinder 10 causes pressurization of a liquid or of a gas in said forward chamber 14 of said cylinder, said liquid or gas thereby being expelled from said anterior chamber 14 through said forward aperture 114 of said inner cylinder tube 110, and then in one exemplary embodiment said liquid or gas being further expelled from said ergonomic suction syringe by means of a port 102, which may in some cases comprise a one-way valve that permits flow of fluid or gas out of said forward chamber 14 to an atmosphere but not in an opposite direction from said atmosphere into said forward chamber 14.

FIG. 10A is an oblique lateral surface view of another exemplary embodiment of an ergonomic suction syringe where a means for transferring vacuum 116 from said back chamber (not shown) to said forward chamber (not shown) comprises an expansion of a side wall of a forward aspect of said cylinder 10, said expansion resulting in a loss of contact of a piston head 18 or a piston head gasket 19 at that region to an inner wall of said cylinder 10, thereby permitting transmission of a vacuum from said back chamber 13 to a forward end of said forward chamber 14 and thereby to a medical device attached thereto. FIG. 10B is an end-on surface view of an ergonomic suction syringe depicted in FIG. 10A.

FIG. 11A is an oblique lateral surface view of another exemplary embodiment of an ergonomic suction syringe where a means for transferring vacuum 116 from said back chamber 13 to said forward chamber 14 comprises a hollow tube securely attached to a forward aspect of said cylinder 10, a long axis of said tube's orientation being essentially in line with a long axis of said cylinder 10, said hollow tube thereby permitting transmission of a vacuum from said back chamber 13 to a forward end of said forward chamber 14 and thereby to a medical device attached thereto. FIG. 11B is an end-on surface view of an ergonomic suction syringe depicted in FIG. 11A.

FIG. 12 is a longitudinal cut-away view of another exemplary embodiment of an ergonomic suction syringe in which a means 116 for transmission of vacuum generated in said back chamber 13 to said forward chamber 14 is an annular expansion of the cross-sectional diameter of a forward aspect of said cylinder 10.

FIG. 13 is a longitudinal cut-away view of another exemplary embodiment of an ergonomic suction syringe in which a means for transmission of vacuum generated in said back chamber 13 to said forward chamber 14 is for said cylinder 10 to possess a variable bore, with enlargement of said bore at a point 117 generally disposed to a forward end of said forward chamber 14 relative to a bore of said cylinder 10 further toward said back end 11.

FIG. 14A and FIG. 14B are an oblique surface views of exemplary embodiments of said piston head gasket 19, said piston head gasket 19 comprising a generally flat disk attached securely to a piston head 18, in this exemplary embodiment further comprising a means for transmission of vacuum from said back chamber 13 to said forward chamber 14, said means comprising a flap valve 43, said flap valve 43 comprising overlapping membranes having an initial closed configuration as shown in FIG. 14A impervious to passage of vacuum across said flap valve 43, and at least a second open configuration as shown in FIG. 14B permitting transmission of vacuum from said back chamber 13 to said forward chamber 14. In one exemplary embodiment, conversion from said closed configuration to said open configuration is actuated when a threshold of vacuum pressure is achieved, said threshold being the level of vacuum at which said flap valve 43 is no longer competent. It can readily be appreciated that said means for transmission could comprise other configurations of one-way valves. It can further be appreciated that a feature of said one-way valves is that they serve as a means of egress for any fluids and gases that may accumulate in said back chamber 13 during use to said forward chamber 14 on a retraction maneuver of said piston 16 after said ergonomic suction syringe has been used to create vacuum in a medical device.

FIG. 15A and FIG. 15B are longitudinal cutaway views of another exemplary embodiment of an ergonomic suction syringe. FIG. 15A depicts an ergonomic suction syringe with a piston 16 advanced to a location such that a piston head 18 is generally disposed toward a forward end of a cylinder 10, but not far enough forward that it interfaces with a means 118 to transmit vacuum from a back chamber 13 to a forward chamber 14. In this exemplary embodiment, with said piston 16 advanced forward in said cylinder 10, there may be vacuum in said back chamber 13. FIG. 15B depicts an exemplary embodiment of an ergonomic suction syringe with said piston 16 advanced further forward in said cylinder 10 such that said piston head 18 is located within said means 118 of transmitting vacuum from said back chamber 13 to said forward chamber 14, thereby to an attached medical device if present. In this embodiment a physical stop 119 is incorporated in the forward chamber that serves to arrest further forward movement of said piston 16 when said piston head 18 is in a location comprising a means 119 of vacuum transmission from said back chamber 13 to said forward chamber 14. Said stop optimally positions said piston head 18 to activate and maintain maximum vacuum, while not allowing said piston head 18 or said piston gasket 19 from contacting a forward end of said forward chamber 14 such that said piston head 18 or said piston head gasket 19 interfere with transmission of vacuum or passage of gases or liquids through a tip adapter 101. One can readily appreciate that there are many configurations of said physical stop 119 that would achieve this purpose.

FIGS. 16A-D illustrate another exemplary embodiment of an ergonomic syringe. FIG. 16A is a longitudinal cutaway view of said ergonomic suction syringe in which said means 118 of transmission of vacuum from said back chamber 13 to said forward chamber 14 comprises a defect 118 in said piston head 18, said defect slidably interfacing with a structural element 120 that runs along an inner aspect of a cylinder 10 wall, generally running longitudinally within said cylinder 10 and having a generally constant cross-sectional shape, in a generally air-tight seal over almost the entire range of motion of said piston head 18 during use, except at a point generally disposed toward a forward end of said forward chamber 14 whereupon said structural element 120 is not present, and whereupon advancement of said piston 16 moves said piston head forward beyond the end of said structural element 120, leaving said defect 118 unplugged, allowing vacuum to be transmitted from said back chamber 13 to said forward chamber 14 through said defect 118. One can readily envision that said defect 118 can have numerous alternative shapes, and FIG. 16B is an exemplary embodiment of an end-on view of said piston head 18 in which said defect 118 generally comprises a circle, or oval, in which case said structural element 120 would have a corresponding cross-section shape. FIG. 16C is an exemplary embodiment of an end-on view of said piston head 18 in which said defect 118 generally comprises a semicircle, in which case said structural element 120 would have a corresponding cross-section shape. FIG. 16D is an exemplary embodiment of an end-on view of said piston head 18 in which said defect 118 comprises a generally rectangular shape, or a square shape, in which case said structural element 120 would have a corresponding cross-section shape.

FIG. 17A and FIG. 17B represent another exemplary embodiment of an ergonomic suction syringe. In this exemplary embodiment, said means of transmitting vacuum from said back chamber 13 to said forward chamber 14 comprises a generally crescent-shaped defect in said piston head 18, in which said structural element 120 in said cylinder 10 would have a corresponding cross-section shape.

INCORPORATION BY REFERENCE

References and citations to other documents, such as patents, patent applications, provisional patent applications, patent publications, journals, books, papers, web content, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

CONCLUSIONS

In summary, the invention disclosed herein comprises an ergonomic suction syringe and method for performing medical procedures in which said ergonomic suction syringe generates suction that can be delivered to a medical device by a single-handed compression motion, with suction actuated by forward motion of a piston into a cylinder, and in which suction can be maintained essentially permanently once activated without any further effort by the operator, even hands-free.

I claim:

1. A method of establishing suction in a lumen of a medical device comprising:
    (a) reversibly attaching an ergonomic suction syringe to said medical device, said ergonomic suction syringe comprising a back end disposed toward an operator and a forward end disposed toward said medical device, said ergonomic suction syringe further comprising a cylinder and a piston, said cylinder further comprising at least an air-tight back chamber disposed toward said back end and a forward chamber disposed toward said forward end, and said piston comprising at least a piston head securely attached to a piston rod, said forward chamber and said back chamber being separated from each other by said piston head, said piston head comprising an air-tight seal between said forward chamber and said back chamber, said piston head occupying a cross-sectional area of an interior of said cylinder, said ergonomic suction syringe further comprising a means of transfer of said vacuum from said back chamber to said forward chamber, and said ergonomic suction syringe further comprising a means of transmission of said vacuum from said forward chamber to a medical device by means of an adapter tip; and
    (b) slidably moving said piston in a forward direction from a first position disposed toward said back end to a second position disposed toward said forward end to generate said vacuum in said back chamber, and
    (c) slidably moving said piston in a further forward direction until said means for vacuum transfer between said back chamber and said forward chamber is actuated, thereby allowing vacuum to be transmitted to said forward chamber and by extension to said attached medical device.

2. The method of establishing suction in a lumen of a medical device of claim 1 wherein said medical device is selected from the group consisting of a needle and an angioplasty balloon catheter.

3. The method of establishing suction in a lumen of a medical device of claim 1 wherein said suction is used to perform a medical procedure s selected from the group consisting of a phlebotomy, an intravenous access placement, a needle biopsy, a needle aspiration of bodily fluid, a vascular access placement, an angioplasty, and a vascular stent placement.

4. The method of establishing suction in a lumen of a medical device of claim 1 wherein said means for vacuum transfer between said back chamber and said forward chamber comprises opening of a communication between said back chamber and said forward chamber.

5. The method of establishing suction in a lumen of a medical device of claim 1 wherein said ergonomic suction syringe further comprises an inner cylinder tube that comprises a secure attachment within said cylinder, said secure attachment disposed toward said forward end within said cylinder, said cylinder tube further comprising an aperture disposed towards said forward end within said cylinder, said piston rod also comprising an aperture, said cylinder tube comprising an outer aspect that interfaces with an inner aspect of said piston rod such that said interface comprises an air-tight seal, wherein said means for vacuum transfer from said back chamber to said forward chamber and by extension to said attached medical device during forward movement of said piston is achieved by said piston rod aperture overlapping at least in part with said inner cylinder tube aperture, thereby allowing communication of vacuum from said back cylinder chamber to said inner aspect of said inner cylinder tube and thereby by extension to said attached medical device by said adapter tip of said ergonomic suction syringe.

6. The method of establishing suction in a lumen of a medical device of claim 1 in which suction achieved by manual force is maintained after release of manual force.

7. The method of establishing suction in a lumen of a medical device of claim 6 in which said suction can be maintained indefinitely.

8. The method of establishing suction in a lumen of a medical device of claim 1 comprising a means to expel compressed gas from said forward chamber when said piston is slidably advanced within said cylinder.

9. The method of establishing suction in a lumen of a medical device of claim 8 wherein said means to expel compressed gas from said forward chamber when said piston is slidably advanced within said cylinder is a one-way valve.

10. The method of establishing suction in a lumen of a medical device of claim 1 wherein manipulation to achieve suction comprises a manual compression motion.

11. The method of establishing suction in a lumen of a medical device of claim 4 wherein said communication comprises a defect in a piston head.

12. The method of establishing suction in a lumen of a medical device of claim 4 wherein said communication selected from the group consisting of pressure-actuated change in configuration of a piston head, pressure-actuated opening of an aperture in a piston head, pressure-actuated opening of a valve in a diaphragm, pressure-actuated failure of a piston head gasket, expansion of at least part of an inner diameter of said forward chamber such that said piston head loses air-tight contact with a forward chamber inner wall when advanced thereto, a conduit or channel external to said forward chamber that allows fluid or gas to bypass said air-tight seal in said piston head when said piston head diaphragm is general disposed in said forward end of said cylinder chamber, an aperture in a hollow piston rod and a corresponding aperture in an inner cylinder tube such that overlapping alignment of said apertures occurs when said piston rod is advanced to a forward end of said cylinder thereby allowing transmission of vacuum therethrough from said back chamber to said forward chamber.

\* \* \* \* \*